United States Patent [19]

Michel et al.

[11] Patent Number: 5,286,648
[45] Date of Patent: Feb. 15, 1994

[54] A84575 ANTIBIOTICS

[75] Inventors: Karl H. Michel, Indianapolis; Raymond C. Yao, Carmel, both of Ind.

[73] Assignee: Eli Lilly and Company, Indianapolis, Ind.

[21] Appl. No.: 722,060

[22] Filed: Jun. 27, 1991

Related U.S. Application Data

[63] Continuation-in-part of Ser. No. 422,185, Oct. 16, 1989, abandoned.

[51] Int. Cl.$^5$ .......................... C12R 1/01; C12N 1/20; C12P 21/04
[52] U.S. Cl. .............................. 435/252.1; 435/71.3; 435/822
[58] Field of Search ..................... 435/252.1, 822

[56] References Cited

U.S. PATENT DOCUMENTS

| | | | |
|---|---|---|---|
| 4,461,723 | 7/1984 | Hershberger et al. | 530/322 |
| 4,558,036 | 12/1985 | Merkel et al. | 530/322 |
| 4,782,042 | 11/1988 | Selva et al. | 530/317 |

OTHER PUBLICATIONS

Waltho et al., "Structure Elucidation of the Glycopeptide Antibiotic Complex A40926," *J. Chem. Soc. Perkin Trans I*, 2103-2107 (1987).

S. B. Christenson et al., "Parvodicin, A Novel Glycopeptide from a New Species *Actinomadura parvosata*: Discovery, Taxonomy, Activity and Structure Elucidation," *J. Antibiotics* 60(7), 970-990 (1987).

F. P. Mertz et al., "Streptosporangeum carneum sp. nov. Isolated from Soil," *Intern. J. Systematic Bacteriol.* 40(3), 247-253 (1990).

SmithKline Beckman Corp., "New Macrocyclic Glycopeptide Antibiotic Complex AAJ-271-Useful Therapeutically and as Animal Feed Additive, and New Actinomadura Parvosata Species," Derwent Abstract 88-030461/05 of EP-255-256-A.

*Primary Examiner*—Herbert J. Lilling
*Attorney, Agent, or Firm*—Paul R. Cantrell; Leroy Whitaker; Nancy J. Harrison

[57] ABSTRACT

Newly discovered lipoglycopeptide antibiotic A84575 complex, comprising factors A, B, C, D, E, F, G, and H, is produced by submerged aerobic fermentation of a culture selected from *Streptosporangeum carneum* NRRL 18437, *Streptosporangeum carneum* NRRL 18505 or an A84575-producing mutant thereof. The antibiotics are active against Gram-positive bacteria.

1 Claim, 6 Drawing Sheets

Dendrogram of A84575 and Streptosporangia Species

A84575 ANTIBIOTICS

This application is a C18 of Ser. No. 07/422,185 filed Dec. 16, 1989, now abandoned.

BACKGROUND OF THE INVENTION

New, improved antibiotics are continually in demand, particularly for the treatment of human diseases. Increased potency, expanded spectrum of bacterial inhibition, increased in vivo efficacy, and improved pharmaceutical properties are some of the goals for improved antibiotics.

One class of antibiotics is the glycopeptide class. The glycopeptide class includes, for example, the known antibiotics vancomycin, parvocidin, actinoidin, and ristocetin. Common to all of these complex antibiotics is the presence of at least one carbohydrate and at least one peptide portion. The A84575 antibiotics are most similar to parvocidin.

SUMMARY OF THE INVENTION

This invention relates to novel lipoglycopeptides. In particular, it relates to the A84575 complex, a complex of at least eight novel lipoglycopeptides called A84575 factors A, B, C, D, E, F, G, and H, which can be separated from each other and isolated as distinct entities.

This invention also relates to a process for producing the A84575 complex, by culturing a novel strain selected from *Streptosporangium carneum* NRRL 18437, *Streptosporangium carneum* NRRL 18505, or an A84575-producing mutant thereof, under submerged aerobic conditions in a suitable culture medium until a substantial amount of the complex is produced and to the novel microorganisms which produce the A84575 complex.

Figure 4:
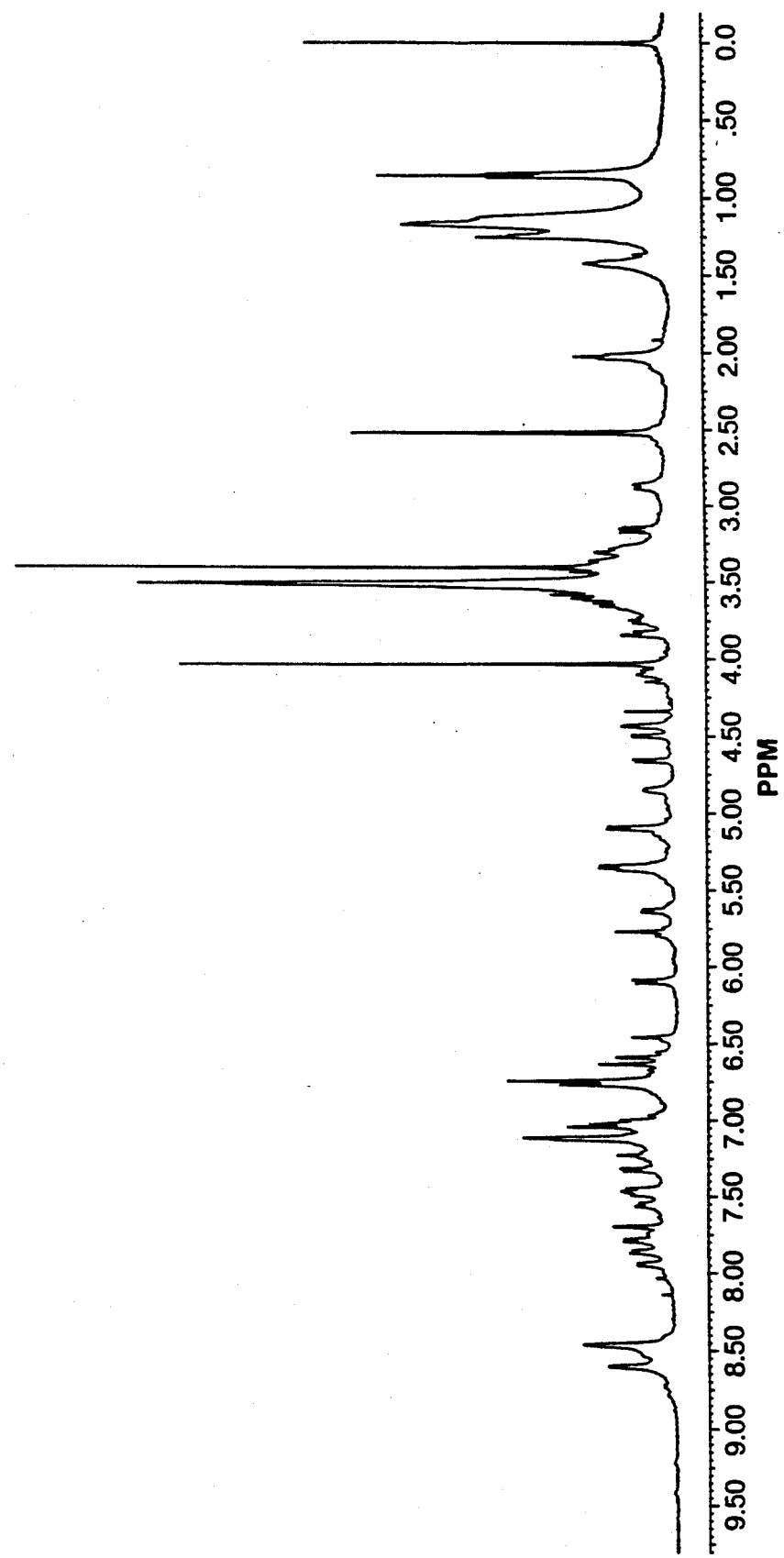
FIG. 4 is a 500 MHz $^1$H NMR spectrum of A84575 Factor A in DMSO-$d_6$.
Figure 5:
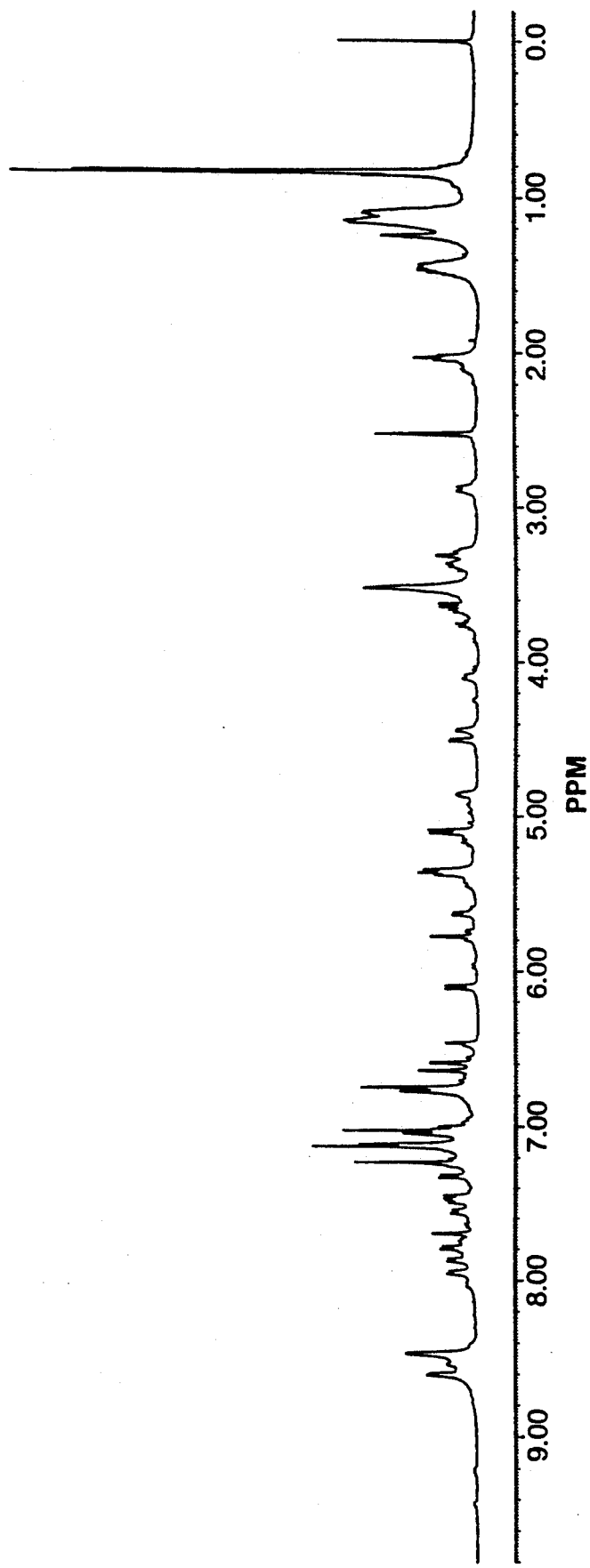
FIG. 5 is a 500 MHz $^1$H NMR spectrum of A84575 Factor B in DMSO-$d_6$.
Figure 6:
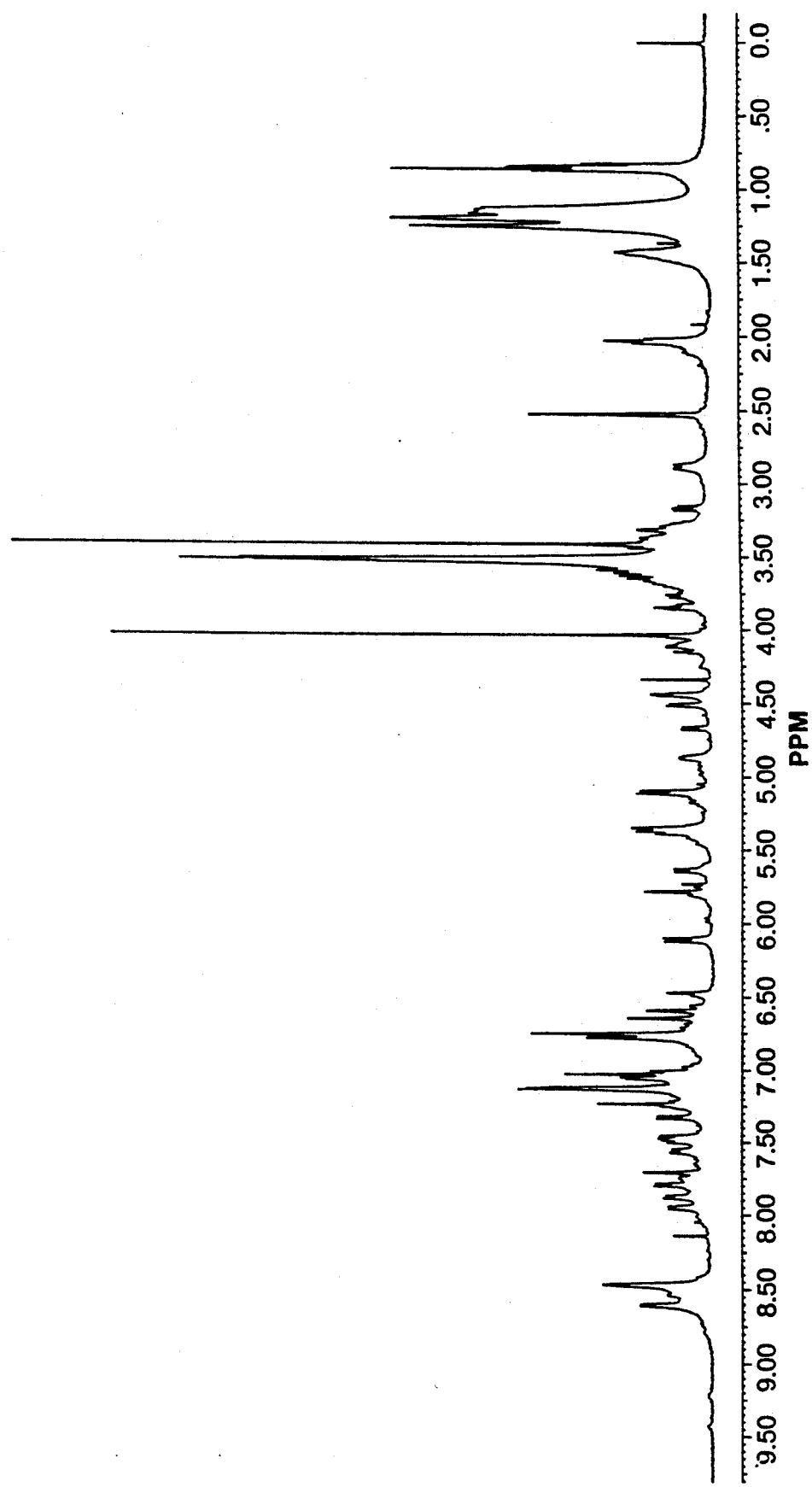
FIG. 6 is a 500 MHz $^1$H NMR spectrum of A84575 Factor C in DMSO-$d_6$.

The NMR's of FIGS. 4, 5, and 6 are in $\delta$ scale and utilize tetramethylsilane as reference (0.0).

DETAILED DESCRIPTION OF THE INVENTION

The A84575 complex, comprised mainly of factors A, B, C, D, E, F, G, and H, is produced by culturing a novel strain selected from *Streptosporangium carneum* NRRL 18437, *Streptosporangium carneum* NRRL 18505, or an A84575-producing mutant thereof, in an aqueous culture medium until the A84575 complex is produced. The individual factors are designated herein as A84575 factors A, B, C, D, E, F, G, and H and can be separated from each other and isolated as distinct entities by methods understood in the art.

The A84575 factors are similar in structure. Each of the factors possesses a terminal amino moiety, thus distinguishing them from the known antibiotic parvocidin. The individual factors have the following physical and biological properties.

A84575 Factor A

A84575 factor A (A84575A) is believed to have the following structure:

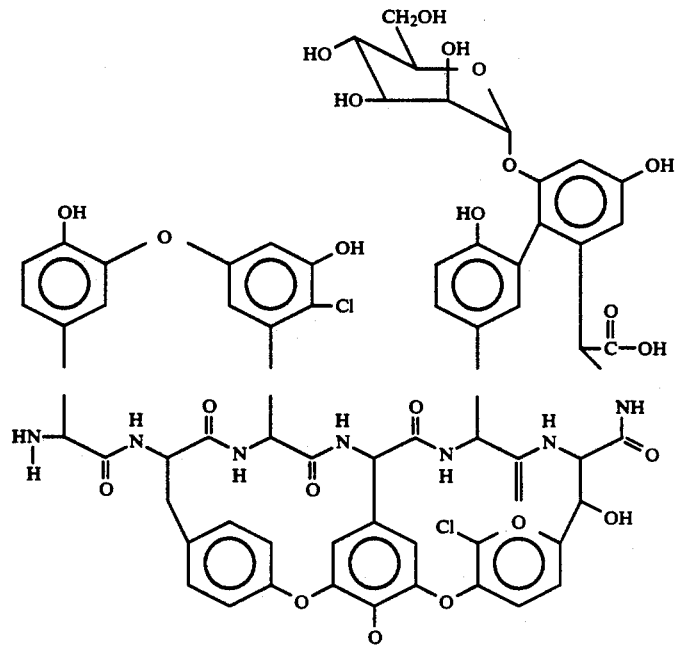

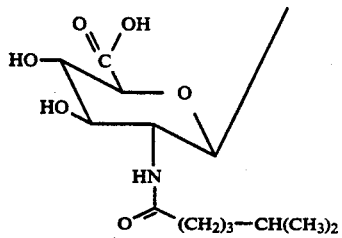

A84575A is a white solid which is soluble in alcohol-water mixtures, dimethyl sulfoxide, dimethylformamide, dimethyl sulfoxide-water mixtures, dimethylformamide-water mixtures and is partially soluble in acidic and basic water solutions.

A84575 has an empirical formula of $C_{80}H_{84}N_8O_{28}Cl_2$ and a molecular weight determined by fast-atom-bombardment mass spectroscopy (FAB MS) to be approximately 1674.

The proton magnetic resonance ($^1$H NMR) spectrum of A84575A at 500 MHz in DMSO-$d_6$ is shown in FIG. 4.

A84575 Factor B

A84575B is a white solid which is soluble in alcohol-water mixtures, dimethyl sulfoxide, dimethylformamide, dimethyl sulfoxide-water mixtures, dimethylformamide-water mixtures and is partially soluble in acidic and basic water solutions.

A84575B has an empirical formula of $C_{81}H_{86}N_8O_{28}Cl_2$ and a molecular weight determined by FAB MS to be approximately 1688.

The ultraviolet spectrum of A84575B revealed a $\lambda(max)=282$ nm in ethanol ($\epsilon=10,404$).

Figure 1:
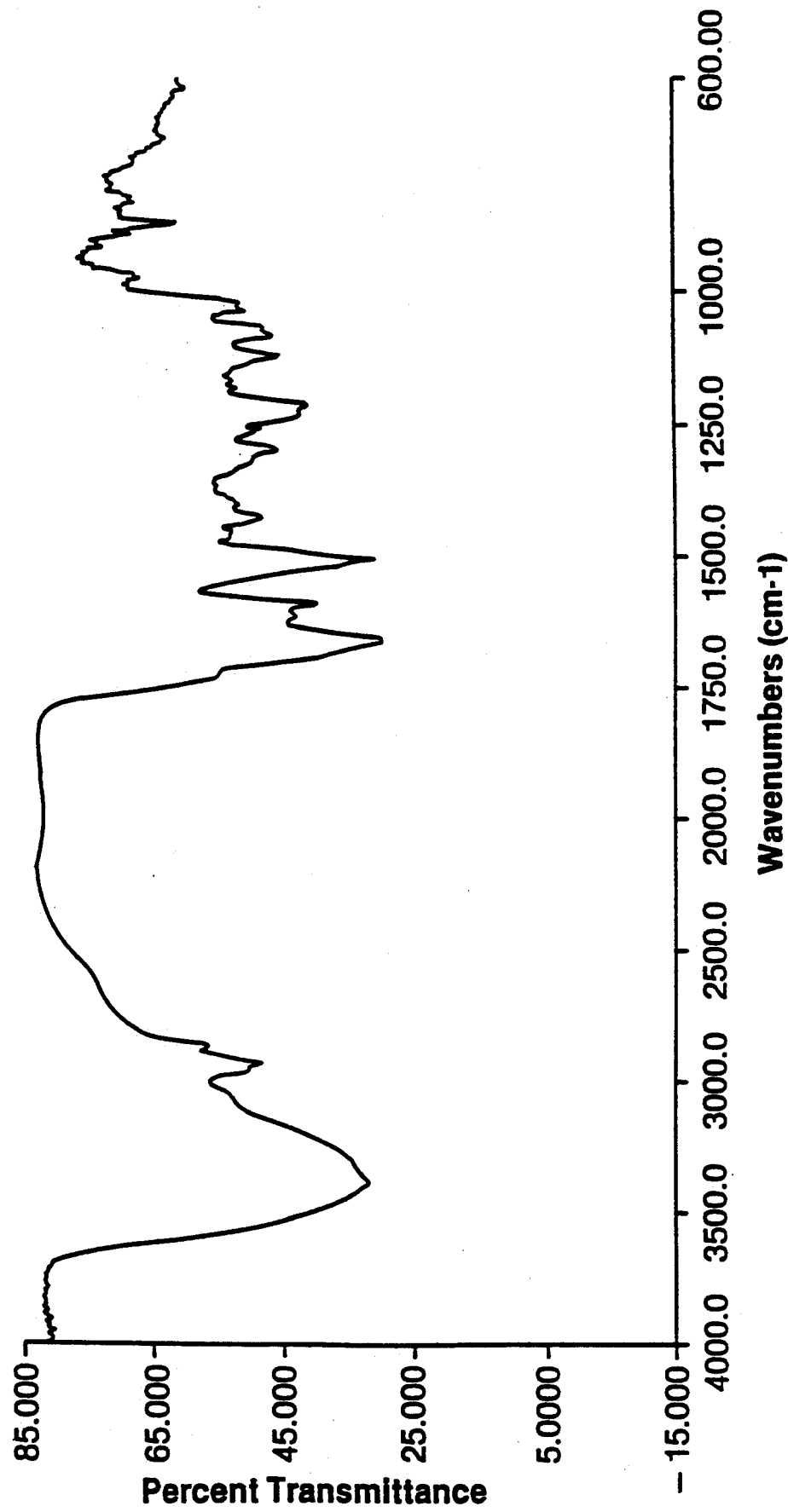
FIG. 1 is an infrared spectrum of A84575 factor B.

The infrared (IR) spectrum of A84575B is shown in FIG. 1 of the drawings. Significant IR absorption maxima include peaks at 3257.4, 1658.0, 1613.4, 1588.8, 1505.8, 1230.4, and 1213.4 cm$^{-1}$.

The $^1$H NMR spectrum of A84575B at 500 MHz in DMSO-$d_6$ is shown in FIG. 5.

A84575 Factor C

A84575C is a white solid which is soluble in alcohol-water mixtures, dimethyl sulfoxide, dimethylformamide, dimethyl sulfoxide-water mixtures, dimethylformamide-water mixtures and is partially soluble in acidic and basic water solutions.

A84575C has an empirical formula of $C_{81}H_{86}N_8O_{28}Cl_2$ and a molecular weight determined by FAB MS to be approximately 1688.

The $^1$H NMR spectrum of A84575C at 500 MHz in DMSO-$d_6$ is shown in FIG. 6.

A84575 Factor D

A84575D is a white solid which is soluble in alcohol-water mixtures, dimethyl sulfoxide, dimethylformamide, dimethyl sulfoxide-water mixtures, dimethylformamide-water mixtures and is partially soluble in acidic and basic water solutions.

A84575D has an empirical formula of $C_{82}H_{88}N_8O_{28}Cl_2$ and a molecular weight determined by FAB MS to be approximately 1702.

A84575 Factor E

A84575E is a white solid which is soluble in alcohol-water mixtures, dimethyl sulfoxide, dimethylformamide, dimethyl sulfoxide-water mixtures, dimethylformamide-water mixtures and is partially soluble in acidic and basic water solutions.

A84575E has an empirical formula of $C_{82}H_{88}N_8O_{28}Cl_2$ and a molecular weight determined by FAB MS to be approximately 1702.

A84575 Factor F

A84575F is a white solid which is soluble in alcohol-water mixtures, dimethyl sulfoxide, dimethylformamide, dimethyl sulfoxide-water mixtures, dimethylformamide-water mixtures and is partially soluble in acidic and basic water solutions.

A84575F has an empirical formula of $C_{82}H_{90}N_8O_{28}Cl_2$ and a molecular weight determined by FAB MS to be approximately 1716.

A84575 Factor G

A84575G is a white solid which is soluble in alcohol-water mixtures, dimethyl sulfoxide, dimethylformamide, dimethyl sulfoxide-water mixtures, dimethylformamide-water mixtures and is partially soluble in acidic and basic water solutions.

A84575G has an empirical formula of $C_{82}H_{90}N_8O_{28}Cl_2$ and a molecular weight determined by FAB MS to be approximately 1716.

A84575 Factor H

A84575H is a white solid which is soluble in alcohol-water mixtures, dimethyl sulfoxide, dimethylformamide, dimethyl sulfoxide-water mixtures, dimethylformamide-water mixtures and is partially soluble in acidic and basic water solutions.

The molecular weight of A84575H was determined by FAB MS to be approximately 1686.

The A84575 factors can be separated and identified conveniently by high performance liquid chromatography (HPLC). The factors have the listed retention times in the following HPLC system:

Column: YMC, AQ-301, 5 µ, ODS, 4.6×100 mm

Mobile Phase: (A) $CH_3CN:H_2O(0.5M$ $NH_4OAc$,pH 5.5)(1:4).

(B) $CH_3CH:H_2O(0.5M$ $NH_4OAc$,pH 5.5)(2:3).

Gradient: A:B (9:1) to A:B (1:3)

Flowrate: 1.5 mL/minute

Detection: UV (280 nm)

| Factor | Retention Time (Minutes) |
|---|---|
| A | 5.85 |
| B | 7.25 |
| C | 7.62 |
| D | 9.00 |
| E | 9.35 |
| F | 10.77 |
| G | 11.07 |

-continued

| Factor | Retention Time (Minutes) |
|---|---|
| H | 6.62 |

A further aspect of the present invention is a biologically purified culture selected from *Streptosporangium carneum* strain NRRL 18437, NRRL 18505, or an A84575-producing a mutant thereof. The NRRL 18437 culture will be referred to herein as culture A84575, and the NRRL 18505 culture as culture A84575.4.

Taxonomic Study of A84575

Culture A84575 was isolated from a soil sample collected by the Tana River in Nairobi, Kenya, Africa.

A84575 produces a lipoglycopeptide antibiotic, which is uncommon for the Streptosporangia.

The following is a characterization of A84575. Data are presented to show that this isolate is a new species for which the name *Streptosporangium carneum* sp. nov. has been selected. This classification is based on the comparison of A84575 with published descriptions of similar species, and on direct laboratory comparisons.

Methods Used

The methods recommended by the International Streptomyces Project (ISP) for the characterization of Streptomyces species were followed (E. B. Shirling and D. Gottlieb, 1966, "Methods for characterization of Streptomyces species", *Int. J. Syst. Bacteriol.*, 16:313-340), as well as methods given by Gordon (R. E. Gordon, D. A. Barnett, J. E. Handerhan, and C. Pang, 1974, "Nocardia coeliaca, Nocardia autotrophica, and the Nocardin strain", *Int. J. Syst. Bacteriol.*, 24:54-63).

ISCC-NBS Centroid Color Charts (U.S. Department of Commerce, National Bureau of Standards, 1958, ISCC-NBS Centroid Color Charts, Standard Sample No. 2106, U.S. Department of Commerce, Washington, D.C.) were used to assign color names to the reverse side. Aerial hyphae were assigned color names from the *Color Harmony Manual* (Container Corporation of America, 1958, *Color Harmony Manual*, 4th ed., Container Corporation of America, Chicago, Ill). Morphology was studied using an optical light microscope and a scanning electron microscope (SEM).

The isomer of diaminopimelic acid (DAP) and the carbohydrates in hydrolysates of whole cells were established by the chromatographic methods of Becker et al. (B. Becker, M. P. Lechevalier, R. E. Gordon, and H. E. Lechevalier, 1964, "Rapid differentiation between Nocardia and Streptomyces by paper chromatography of whole-cell hydrolysates", *Appl. Microbiol.*, 12:421-423) and of Lechevalier (M. P. Lechevalier, and H. Lechevalier, 1970, "Chemical composition as a criterion in the classification of aerobic actinomycetes", *Int. J. Syst. Bacteriol.*, 20:435-443), respectively.

Phospholipids were determined by the procedure of the Lechevaliers (M. P. Lechevalier and H. Lechevalier, 1980, "A University Laboratory Approach", Dietz and Thayer (eds.), Society for Industrial Microbiology Special Publication No. 6, Arlington, Va., p. 227-233).

Menaquinone composition was determined by following the procedures of R. M. Kroppenstedt [in *Chemical Methods in Bacterial Systematics*, M. Goodfellow and D. E. Minnikin (eds.), p. 173-196, 1985] and M.D. Collins (ibid, p. 267-285).

Resistance to antibiotics was measured by padding antibiotic sensitivity discs (Difco) onto the surface of seeded ISP No. 2 agar plates. Resistance was scored as (+) when no zone of inhibition was observed, and as (−) when a zone of inhibition was observed.

Fatty acid analysis was done using the HP 5898A Microbial Identification System (L. Miller and T. Berger, 1985, "Bacterial identification by gas chromatography of whole cell fatty acids", Hewlett-Packard Application Note 228-41, 8 pp.). Fatty acid methyl esters were made from lyophilized whole cells grown under identical conditions.

Mycolic acids were analyzed using the methods proposed by Minnikin et al. (D. E. Minnikin, I. G. Hutchinson and A. B. Caldicott, 1980, "Thin-layer chromatography of methanolysates of mycolic acid-containing bacteria", *J. Chromatography*, 188:221-233).

Cultural Characteristics

A84575 grew well on both complex and defined media. Aerial hyphae were produced on most of the media used. Abundant sporangia formation was observed on many of the media. The aerial spore mass was predominately light yellowish-pink (flesh pink; pale peach); however, pale orange-yellow was also observed. The reverse side was mainly orange in color. Light brown soluble pigment was observed in 3 of 18 media used. The cultural characteristics of culture A84575 are presented in Table 1. ANIO-HENSENS, BENNETTS, CZAPEKS, EMERSONS, and MUELLER-HINTON are standard growth media known to those skilled in the art.

TABLE 1

Cultural characteristics of A84575[1]

| Medium | Growth | Reverse Color | Aerial Mycelium Growth | Aerial Mycelium Color | Soluble Pigment |
|---|---|---|---|---|---|
| ISP medium 2 | Abundant | 55.s. Brown | Abundant* | 3ca p.O. Yellow | None |
| ISP medium 3 | Fair | 73.p.O. Yellow | Fair* | 3ca p.O. Yellow | None |
| ISP medium 4 | Good | 73.p.O. Yellow | Good* | 5ca l.y. Pink | None |
| ISP medium 5 | Good | 52.l. Orange | Fair | 5ca l.y. Pink | None |
| ISP medium 7 | Good | 53.m. Orange | Good | 5ca l.y. Pink | l.r. Brown |
| ATCC No. 172 | Good | 53.m. Orange | Abundant* | 5ca l.y. Pink | None |
| ANIO-HENSENS | Good | 53.m. Orange | Good* | 5ca l.y. Pink | None |
| BENNETTS | Good | 53.m. Orange | Good | 5ca l.y. Pink | None |
| Calcium malate | Fair | 77.m.y. Brown | Fair* | 5ca l.y. Pink | None |
| Chitin | Good | 53.m. Orange | Good* | 5ca l.y. Pink | None |
| CZAPEKS | Good | 51.d. Orange | Good* | 5ca l.y. Pink | None |
| EMERSONS | Abundant | 40.s.r. Brown | Fair | 5cb gy.y. Pink | l. Brown |
| GAA[2] | Good | 40.s.r. Brown | Fair | 5ca l.y. Pink | None |
| Glycine | Poor | 51.d. Orange | None | None | None |
| Nutrient Agar | Fair | 54.br. Orange | Fair | 5ca l.y. Pink | None |
| TPO[3] | Abundant | 72.d.O. Yellow | Good | 5ca l.y. Pink | None |

TABLE 1-continued

| | | Cultural characteristics of A84575[1] | | | |
|---|---|---|---|---|---|
| | | Reverse | Aerial Mycelium | | Soluble |
| Medium | Growth | Color | Growth | Color | Pigment |
| TWA[4] | Fair | 90.gy. Yellow | Fair* | 5cb gy.y. Pink | None |
| YDA[5] | Abundant | 58.m. Brown | Trace | 5ca l.y. Pink | r. Brown |

*Abundant sporangia formation
[1]Incubated at 30° C. for 21 days
[2]Glucose Asparagine Agar
[3]Tomato Paste Oatmeal Agar
[4]Tap Water Agar
[5]Yeast Dextrose Agar

Morphological Characteristics

A84575 produces an extensive non-fragmenting substrate mycelium. Well formed aerial hyphae are present on most of the media. Many globose sporangia were formed from the aerial hyphae. Sporangiophores appear to be of moderate length. The sporangia ranged in diameter from 3 to 9 μm and contained many large spherical spores that averaged 1.3 μm in diameter. When the spores were released they were non-motile.

Physiological Characteristics

Culture A84575 produced acid from cellobiose, fructose, galactose, glucose, lactose, mannose, and trehalose. The culture did not produce acid from adonitol, D- and L-arabinose, cellulose, dextrin, dulcitol, ethanol, erythritol, glycerol, glycogen, inositol, inulin, maltose, mannitol, melizitose, melebiose, α-methyl-D-glucoside, raffinose, rhamnose, ribose, salicin, sorbitol, sorbose, sucrose, xylitol, and xylose.

The culture used the following organic acids (as sodium salts): acetate and pyruvate. It did not use benzoate, butyrate, citrate, formate, lactate, malate, mucate, oxalate, propionate, succinate, and tartrate.

A84575 decomposed casein, hippurate, testosterone, and tyrosine. It did not decompose adenine, allantoin, calcium malate, elastin, esculin, guanine, hypoxanthine, starch, urea, and xanthine.

A84575 produced catalase, phosphatase, and $H_2S$. It was unable to liquefy gelatin, produce melanoid pigments, reduce nitrate, hydrolyze or peptonize milk, nor was it able to survive 50° C. for 8 hours. A84575 tolerated levels of NaCl up to 2%. It grew at temperatures between 20° C. and 37° C.

A84575 was resistant to bacitracin (10 units), cephalothin (30 μm), gentamicin (10 μm), lincomycin (2 μm), penicillin G (10 units), streptomycin (10 μm), tetracycline (30 μm), and tobramycin (10 μm). It was sensitive to neomycin (30 μm), oleandomycin (15 μm), rifampin (5 μm), and vancomycin (30 μm). It was also sensitive to lysozyme (50 μg/mL).

Cell-Wall Analysis

Hydrolyzed whole cells contain mesodiaminopimelic acid. Diagnostic sugars in the whole cell hydrolysates are mannose, arabinose, and madurose. Phospholipid preparations contained phosphatidyl inositol, diphosphatidyl glycerol, and unknown glucosamine-containing phospholipids. Therefore, A84575 has a type III cell wall (Lechevalier, M. P., and H. Lechevalier, 1970, "Chemical composition as a criterion in the classification of aerobic actinomycetes", *Int. J. Syst. Bacteriol.*, 20:435–443) with a type B whole cell sugar pattern, and a type PIV phospholipid composition (Lechevalier, M. P., A. E. Stern, and H. A. Lechevalier, 1981, "Phospholipids in the taxonomy of Actinomycetes", Schaal, K. P., and G. Pulverer (eds): Actinomycetes, Zbl. Bakt. Suppl. 11, Gustav Fischer Verlag, Stuttgart, New York).

The major menaquinones detected were MK-9($H_4$), and a minor amount of MK-9($H_2$).

Identity of A84575

The cell-wall chemistry and the distinctive morphological feature of large sporangia containing non-motile spores are characteristics of, and indicate that A84575 belongs to, the genus Streptosporangium [J. N. Couch and C. E. Bland, 1974, "Key to the species of genus Streptosporangium", p. 712–715, in *Bergey's Manual of Determinative Bacteriology*, R. E. Buchanan and N. E. Gibbons (eds.), The Williams and Wilkins Company, Baltimore; and M. Goodfellow and T. Cross, 1984, in *The Biology of the Actinomycetes*, M. Goodfellow, M. Mordarski, and S. T. Williams (eds), p. 114–115, Academic Press, Inc., Orlando, Fla. 32887.

The keys of Nonomura [H. Nonomura, 1974, "Key for classification and identification of species of rare actinomycetes isolated from soils in Japan", *J. Ferment. Technol.*, 52:71–77; and H. Nonomura and Y. Ohara, 1969, "Distribution of actinomycetes in soil. (VII) A culture method effective for both of preferential isolation and enumeration of Microbispora and Streptosporangium strains in soil. (Part 2) Classification of the isolates", *J. Ferment. Technol.*, 47(11): similar to *S. roseum* and *S. vulgare*. Therefore, comparisons were made with these species.

Table 2 compares differences between A84575 and *S. roseum* and *S. vulgare*.

TABLE 2

| Properties Differentiating A84575 from *S. roseum* and *S. vulgare*. | | | |
|---|---|---|---|
| Property | A84575 | *S. roseum* | *S. vulgare* |
| Starch hydrolysis | − | + | + |
| Nitrate reduction | − | + | + |
| Utilization of: | | | |
| glycerol | − | + | + |
| arabinose | − | + | + |
| rhamnose | − | + | + |
| inositol | − | + | + |
| Gelatin liquefied | − | + | + |
| Milk peptonized | − | + | + |
| Active vs. *S. aureus* | + | − | − |
| Soluble pigment | − | + | − |

Table 3 gives the key features from a fatty acid analysis of these three species.

TABLE 3

| Fatty Acid Analysis of A84575, *S. roseum* and *S. vulgare*. | | | |
|---|---|---|---|
| Fatty Acid | A84575 | *S. roseum* | *S. vulgare* |
| 14:0 ISO | 3.45 | 17.75 | 8.64 |
| 14:0 | 6.86 | 0.42 | 0.52 |
| 15:0 | 2.28 | 7.10 | 10.60 |

TABLE 3-continued

Fatty Acid Analysis of A84575, *S. roseum* and *S. vulgare*.

| Fatty Acid | A84575 | S. roseum | S. vulgare |
|---|---|---|---|
| 16:1 ISO H | — | 1.75 | 0.76 |
| 16:0 ISO | 3.44 | 28.11 | 10.00 |
| 16:0 | 25.21 | 2.01 | 4.67 |
| 17:1 ISO G | 19.41 | 2.10 | 1.09 |
| 18:1 ISO F | 6.93 | 26.57 | 15.33 |
| 18:0 10 Me TSBA | 4.03 | — | 0.45 |

The 16:0 vs. 16:0 ISO fatty acid content and the presence of tuberculostearic acid (10 Me TSBA) clearly distinguish A84575 from the other two species.

A number of other Streptosporangia species have pink aerial masses. Shearer et al. (M. C. Shearer, P. M. Colman and C. H. Nash, 1983, "*Streptosporangium fragile* sp. nov.", *Int. J. Syst. Bacteriol.*, 33:364-368) in their description of *S. fragile* published a table comparing the traits of this particular group. Table 4 compares that data with the data for culture A84575. As Table 4 shows, culture A84575 does not match others in the group having pink aerial masses.

TABLE 4

Comparison of Strain A84575 with Streptosporangia Species Having Pink Aerial Masses.[1]

| Organism | Color of substrate mycelium | Color of soluble pigment | Shape of spores | Growth at 42° C. | Nitrate reduction | Starch hydrolysis | Iodinin production |
|---|---|---|---|---|---|---|---|
| A84575 | Orange to yellow-brown | None | Oval | — | — | — | — |
| S. fragile | Dark brown to black | Brown | Oval | + | + | + | — |
| S. amethystogenes | Yellow-brown | Yellow-brown | Oval | — | + | + | + |
| S. lingisporum | Red to brown-red | None | Cylindrical | — | ± | + | — |
| S. nondiastaticum | Orange | Yellow-brown | Oval | + | + | — | — |
| S. pseudovulgare | Orange to yellow brown | Yellow-brown | Oval | + | + | + | — |
| S. roseum | Red-brown to yellow-brown | Red-brown to purple brown | Spherical | — | + | + | — |
| S. violaceochromogenes | Yellow to orange | Violet | Oval | — | + | + | — |
| S. vulgare | Yellow to pale orange | Yellow to pale orange | Oval | — | — | + | — |

[1]Data taken from Table 1 in Shearer et al. supra.

All of the available Streptosporangia species, i.e., all the species listed in the *Approved Lists of Bacterial Names* (V. B. D. Skerman, V. McGowan, and P. H. A. Sneath, 1980, American Society for Microbiology, Washington, D.C.) plus others known to be validly published were grown under identical conditions and submitted to fatty acid analysis (*S. longisporum* did not grow in the medium used for the other species and, therefore, was grown in a different media.) Eighteen species were compared with each other and with A84575.

Figure 2:
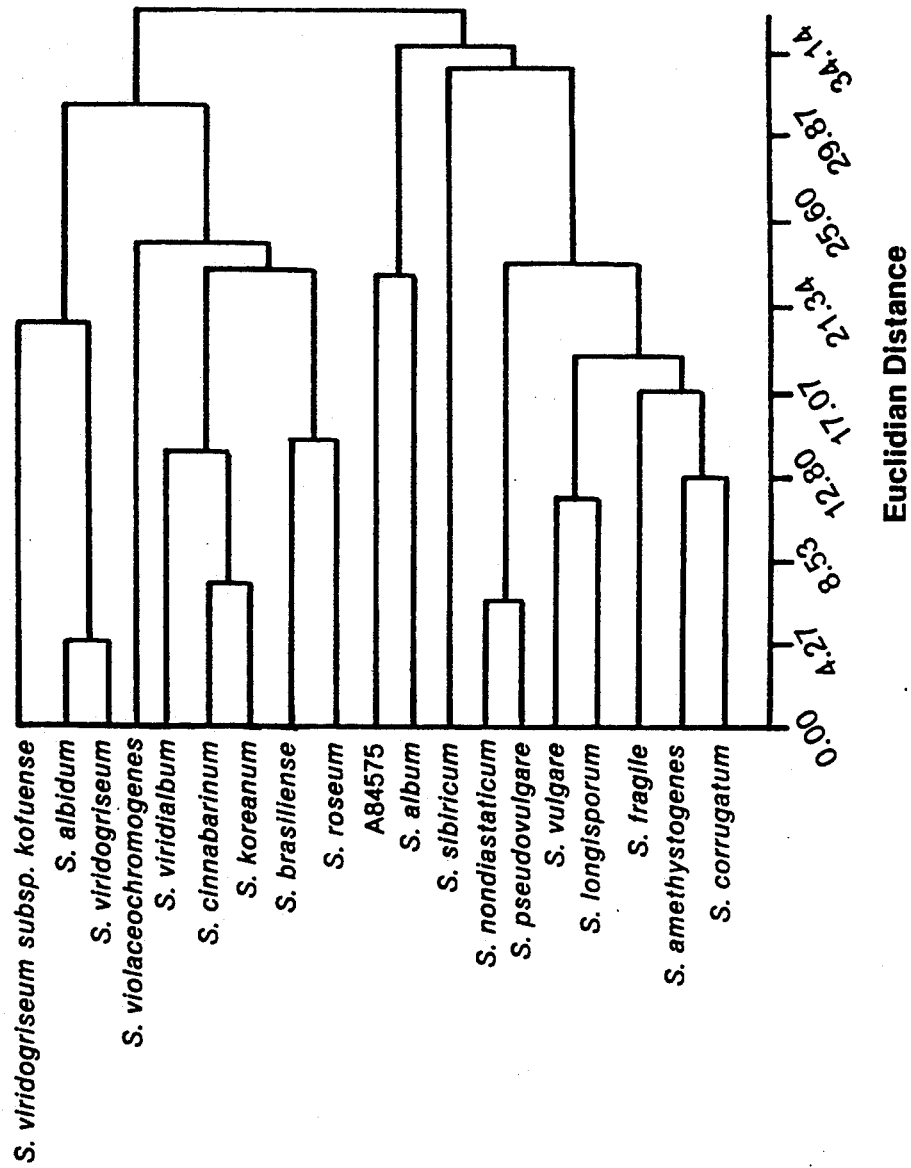
FIG. 2 is a dendrogram of A84575 and selected Streptosporangia species.

FIG. 2 is a dendrogram of the data from this study, showing relationships measured in Euclidian distance. Organisms grouping below a Euclidian distance of 10 are similar enough to be the same species. The closest species to A84575 is *S. album;* however, the Euclidian distance between them is greater than 20.

Figure 3:
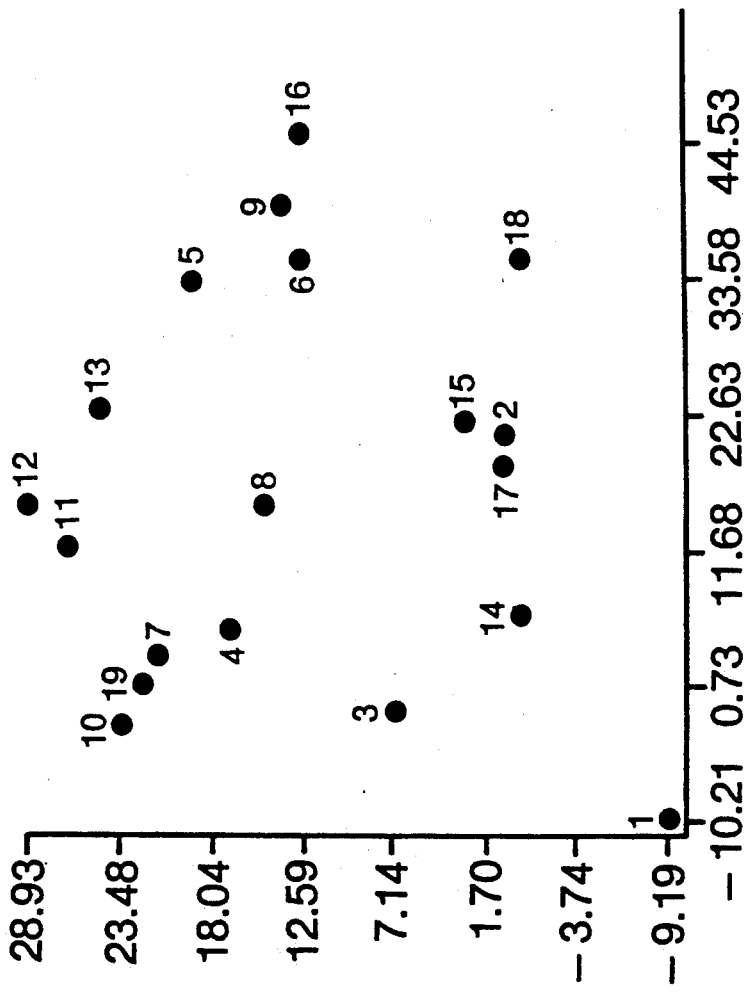
FIG. 3 is a principal component plot of fatty acids from A84575 and selected Streptosporangia species.

FIG. 3 is a principal component plot of fatty acids from A84575 and selected Streptosporangia species. The principle component analysis was two-dimensional and computer-generated. Units of measurement in the principle component plot are standard deviations. Two other plots using different principal components were also done and indicated the same heterogeneity. The Streptosporangia are a very diverse group, and A84575 is not closely related to any of the species included in this study.

A library of fatty acid profiles was generated by computer for the Streptosporangia species. When A84575 was run against these profiles as an unknown, it did not match any existing entry.

Because A84575 is unlike previously described species of Streptosporangia, it is proposed as a new species for which the name *Streptosporangium carneum* has been selected. The species name, *carneum*, means flesh-colored and refers to the color of the aerial mass.

Another useful *Streptosporangium carneum* culture of this invention, culture A84575.4, is a natural variant of the A84575 culture.

The *Streptosporangium carneum* cultures A84575 and A84575.4 have been deposited and made part of the culture collection of the Northern Regional Research Division, U.S. Department of Agriculture, Agricultural Research Service, Peoria, Ill. 61604. The cultures are available under the accession numbers NRRL 18437 (A84575) and NRRL 18505 (A84575.4). The NRRL 18437 culture was deposited on Jan. 12, 1989; and the NRRL 18505 culture was deposited on Jun. 6, 1989.

This invention also relates to a process for producing an antibiotic selected from the A84575 complex, A84575A, A84575B, A84575C, A84575D, A84575E, A84575F, A84575G or A84575H, which comprises cultivating *Streptosporangium carneum* NRRL 18437, NRRL 18505, or an A84575-producing mutant thereof in a culture medium containing assimilable sources of carbon, nitrogen, and inorganic salts, under submerged aerobic fermentation conditions until the antibiotic is produced, optionally followed by separation of the antibiotic from the fermentation medium and/or salification of the antibiotic if not in salt form.

The A84575 antibiotic activity is generally associated with the broth. Thus, the A84575 complex is most readily separated from the fermentation mixture by removing the mycelia (the biomass) by filtration and washing the biomass with water.

The A84575 complex can be separated from the filtered broth/biomass-wash mixture by a number of methods. A convenient method is to adsorb it on a porous resin. The antibiotic can be isolated from the resin by eluting it with polar solvents, such as methanol: water, combining the bioactive fractions and concentrating the resultant solutions to precipitate the A84575 complex.

The A84575 complex can be used directly as an antibacterial agent. Alternatively, the complex can be further purified and separated into its individual factors by well known chromatographic techniques such as thin-layer chromatography, column chromatography, and especially various HPLC procedures.

A number of different media may be used to produce the A84575 complex. For economy in production, optimal yield, and ease of product isolation, however, certain culture media are preferred. These media should contain assimilable sources of carbon, nitrogen, and inorganic salts. Suitable carbon sources include glucose, starch, maltose, fructose, and glycerol. Optimum levels of carbon sources are from about 2 to about 5 percent by weight.

Preferred nitrogen sources include acid digest of soybeans, acid or enzymatic digests of casein, ammonium salts, nitrate salts, glycine, alanine, serine, asparagine, and glutamine.

Essential trace elements necessary for the growth and development of the organism may occur as impurities in other constituents of the media in amounts sufficient to meet the growth and biosynthetic requirements of the organism. However, it may be beneficial to incorporate in the culture media additional soluble nutrient inorganic salts capable of yielding sodium, potassium, magnesium, calcium, ammonium, ferrous, chloride, carbonate, phosphate, sulfate, nitrate, and like ions.

Although small quantities of the A84575 antibiotic may be obtained by shake-flask culture, submerged aerobic fermentation in stirred bioreactors is a preferred method for producing substantial quantities of the A84575 antibiotic. For stirred bioreactor fermentation, it is preferable to use a vegetative inoculum. The vegetative inoculum is prepared by inoculating a small volume of culture medium with submerged culture stocks preserved by storage in the vapor phase of liquid nitrogen, to obtain a fresh, actively growing culture of the organism. The vegetative inoculum is then transferred to a larger bioreactor where, after a suitable incubation time, the A84575 antibiotic is produced in optimal yield.

The A84575-producing organisms produce the A84575 complex over a temperature range of from about 23° to about 37° C. Optimum production of A84575 complex appears to occur at a temperature of about 30° to about 32° C.

As is customary in aerobic submerged culture processes, sterile air is dispersed through the culture medium. For efficient growth of organism, the volume of air used in tank production is in the range of from about 0.1 to about 0.5 volumes of air per volume of culture medium per minute (v/v/m), with from about 150 to about 200 RPM agitation. An optimum rate in a 165-liter vessel containing 115 liters of fermentation medium is about 0.125 v/v/m, with agitation provided by an impeller rotating at about 160 RPM, which is sufficient to maintain the level of dissolved oxygen at or above 40% of air saturation.

The fermentation generally produces antibiotic activity after about 40 hours. Peak antibiotic production occurs at >160 hours fermentation time.

Production of the A84575 antibiotic can be monitored during the fermentation by several methods. Especially useful methods are: agar diffusion assay using *Bacillus subtilis* ATCC 6633, turbidimetric assay using *Staphylococcus aureus* ATCC 9114 or HPLC.

Treatment of the whole broth according to methods disclosed in U.S. Patent Nos. 4,332,406; 4,461,723; and 4,558,036, incorporated herein by reference (pH 10.5, centrifuge, and neutralize) was found to release a three to four-fold additional yield of the A84575 complex.

The A84575 complex and the individual A84575 factors are antibacterial agents and are especially active against Gram-positive microorganisms, as illustrated by the in vitro and in vivo test data in Tables 5-19, which follow. The tables summarize the minimum inhibitory concentrations (MIC) in mcg/mL observed for the test compound vs. the listed organism.

TABLE 5

In Vitro Antibacterial Activity of A84575 Factors

| | Staphylococcus | | | | epi[1] | | Streptococcus | | | | Haemophilus | |
| | aureus | | | | | A | pn[2] | D | | influenzae | |
| | X1.1 | U41 | X400 | S13E | 270 | 222 | C203 | PARK | X66 | 2041 | C.L.[3] | 76[4] |
|---|---|---|---|---|---|---|---|---|---|---|---|---|
| Standard[5] | 2. | 4. | 128. | +16. | 8. | 2. | .015 | .015 | 128.+ | 128. | .015 | .015 |
| A84575C | .5 | 1. | 2. | 1. | 2. | 1. | .125 | .25 | 1. | 2. | 32. | 32. |
| A84575B | .25 | 1. | 1. | .5 | 2. | 1. | .06 | .25 | 1. | 2. | 32. | 32. |
| A84575F | .25 | .5 | 1. | .5 | 2. | 1. | .015 | .03 | .125 | .25 | 32. | 64. |
| A84575 Complex | .25 | 1. | 1. | .5 | 2. | 1. | .03 | .125 | .5 | 1. | 32. | 64. |

[1] *S. epidermidis*
[2] *S. pneumoniae*
[3] sensitive strain
[4] resistant strain
[5] 7-(4-aminothiazol-2-yl)-2-methoxyiminoacetylamino-3-acetoxymethyl-3-cephem-4-carboxylic acid (Claforan)

TABLE 6

Comparison of In Vitro Activity of A84575B and Vancomycin vs. *Staphylococcus aureus* Strains[1]

| | MIC (μg/mL) | |
| Strain | A84575B | Vancomycin |
|---|---|---|
| 3055 | 1.0 | 1.0 |
| 3136 | 1.0 | 1.0 |
| 25923 | 2 | 2 |
| V92 | 0.5 | 0.5 |
| 3123 | 1.0 | 1.0 |
| 3128 | 0.5 | 1.0 |
| 3109 | 1.0 | 1.0 |
| 3110 | 0.5 | 0.5 |
| H290 | 0.5 | 1.0 |
| H535 | 1.0 | 0.5 |
| DUTT* | 1.0 | 0.5 |
| 3131* | 0.5 | 0.5 |
| 3484A* | 1.0 | 1.0 |
| Seattle 973* | 0.5 | 0.5 |
| BGB #10* | 1.0 | 1.0 |
| CVT#6* | 0.5 | 0.5 |
| ID-VI #1* | 0.5 | 0.5 |

TABLE 6-continued
Comparison of In Vitro Activity of A84575B and Vancomycin vs. *Staphylococcus aureus* Strains[1]

| Strain | MIC (μg/mL) | |
|---|---|---|
| | A84575B | Vancomycin |
| #43* | 1.0 | 0.5 |

[1]Agar-dilution method, using MUELLER-HINTON agar
*Methicillin-resistant strain

TABLE 7
Comparison of In Vitro Activity of A84575B and Vancomycin vs. *Staphylococcus epidermidis* Strains[1]

| Strain | MIC (μg/mL) | |
|---|---|---|
| | A84575B | Vancomycin |
| ST-216 | 1.0 | 1.0 |
| 1202-18 | 2 | 2 |
| 50766 | 0.5 | 1.0 |
| 48989 | 2 | 1.0 |
| 3078 | 2 | 1.0 |
| S-3 | 2 | 2 |
| 3079 | 2 | 2 |
| 48213 | 2 | 2 |
| 49030 | 2 | 2 |
| 49536 | 2 | 1.0 |
| ST-214* | 1.0 | 0.5 |
| ST-215* | 2 | 2 |
| ST-217* | 2 | 1.0 |
| ST-220* | 8 | 1.0 |
| ST-222* | 0.5 | 0.5 |
| 12477* | 2 | 2 |
| 49128* | 2 | 1.0 |
| 10-S-81* | 2 | 1.0 |

[1]Agar-dilution method, using MUELLER-HINTON agar
*Methicillin-resistant strain

TABLE 8
Comparison of In Vitro Activity of A84575B and Vancomycin vs. *Streptococcus sp.* (Group D) Strains[1]

| Strain | MIC (μg/mL) | |
|---|---|---|
| | A84575B | Vancomycin |
| 282 | 0.5 | 1.0 |
| Shrigley | 0.5 | 2 |
| 8043 | 0.5 | 1.0 |
| 9901 | 0.5 | 2 |
| 9913 | 0.5 | 1.0 |
| 9933 Beta | 0.5 | 4 |
| M10 | 1.0 | 4 |
| M11 | 0.5 | 1.0 |
| M12 | 0.5 | 4 |
| M13 | 0.5 | 2 |
| M20 | 0.5 | 1.0 |
| M21 | 1.0 | 4 |
| M28 | 0.5 | 4 |
| M36 | 0.5 | 4 |
| M38 | 0.5 | 1.0 |
| 9960 | 1.0 | 4 |
| 12253F | 1.0 | 1.0 |
| Van Almen | 0.5 | 4 |
| Vietnam | 1.0 | 2 |
| 22521 | 1.0 | 4 |

[1]Agar-dilution method, using MUELLER-HINTON agar

TABLE 9
Comparison of In Vitro Activity of A84575B and Vancomycin vs. Miscellaneous *Streptococcus* Strains[1]

| Strain | MIC (μg/mL) | |
|---|---|---|
| | A84575B | Vancomycin |
| *S. salivarius* S262 | 0.25 | 1.0 |
| *S. sanguis* I-SSI-910 | 0.125 | 0.5 |
| *S. sanguis* I-SSI-547 | 0.125 | 0.5 |

TABLE 9-continued
Comparison of In Vitro Activity of A84575B and Vancomycin vs. Miscellaneous *Streptococcus* Strains[1]

| Strain | MIC (μg/mL) | |
|---|---|---|
| | A84575B | Vancomycin |
| *S. sanguis* II-SSII-895 | 0.5 | 0.5 |
| *S. sanguis* II-SSII-911 | 0.25 | 1.0 |
| *S. mutans* SM-1122 | 0.5 | 1.0 |
| *S. mutans* SM-1134 | 4 | 2 |

[1]Agar-dilution method, MUELLER-HINTON Agar

TABLE 10
Comparison of In Vitro Activity of A84575B and Vancomycin vs. *Streptococcus pneumoniae* Strains[1]

| Strain | MIC (μg/mL) | |
|---|---|---|
| | A84575B | Vancomycin |
| Park I | 0.25 | 0.5 |
| HZ-4-2 | 0.125 | 0.25 |
| ATCC 6301 | 2 | 4 |
| 2764 | 0.25 | 0.25 |
| 97P | 0.25 | 0.25 |
| BI5 | 0.5 | 0.5 |
| BI343 | 0.25 | 0.25 |
| BI374 | 2 | 4 |
| BI348 | 0.25 | 0.25 |
| BI508 | 0.25 | 0.5 |
| BI180351 | 0.25 | 0.25 |
| M11-Z-Al | 0.25 | 0.25 |
| M11-1-H7 | 0.25 | 0.5 |
| M11-1-H10 | 0.25 | 0.25 |
| BI-492 | 0.5 | 0.5 |

[1]Agar-dilution method, MUELLER-HINTON agar

TABLE 11
Comparison of In Vitro Activity of A84575B and Vancomycin vs. *Streptococcus pyogenes* Strains[1]

| Strain | MIC (μg/mL) | |
|---|---|---|
| | A84575B | Vancomycin |
| C203 | 0.125 | 1.0 |
| ATCC 12344 | 4 | 1.0 |
| 9931 | 0.125 | 0.5 |
| K-1 | 0.25 | 0.5 |
| K-2 | 0.25 | 0.5 |
| K-3 | 0.25 | 0.5 |
| K-5 | 2 | 1.0 |
| K-6 | 0.5 | 0.5 |
| 10389 | 0.125 | 0.5 |
| DS663-72 | 0.125 | 0.5 |
| 12385 | 0.5 | 2 |
| 12961 | 0.25 | 1.0 |
| HB93 | 2 | 1.0 |
| K-4 | 0.5 | 1.0 |

[1]Agar-dilution method, MUELLER-HINTON agar

TABLE 12
Comparison of In Vitro Activity of A84575B and Vancomycin vs. *Hemophilus influenza* Strains[1]

| Strain | MIC (μg/mL) | |
|---|---|---|
| | A84575B | Vancomycin |
| Astes | 64 | 64 |
| Johnson | 64 | 64 |
| Bond | 64 | 64 |
| Newton | 64 | 64 |
| Bruno | 128 | 128 |
| Lawrence | 64 | 64 |
| Harper | 64 | 64 |
| Lassig | 64 | 32 |

[1]Using broth-dilution method and testing the strains with Shadler broth +5% fildes extract

TABLE 13

SUSCEPTIBILITY OF ANAEROBIC BACTERIAL ISOLATES*

| ANAEROBIC BACTERIA | MIC (μg/mL) | | | | |
|---|---|---|---|---|---|
| | Vancomycin | A84575+ | A84575+ | A84575+ | A84575F |
| *Clostridium difficile* 2994 | 2 | 0.25 | 0.25 | 0.25 | 0.25 |
| *Clostridium perfringens* 81 | 1.0 | 0.5 | 0.5 | 0.5 | 0.5 |
| *Clostridium septicum* 1128 | 2 | ≦0.125 | 0.25 | 0.5 | 0.25 |
| *Eubacterium aerofaciens* 1235 | 8 | 1.0 | 2 | 1.0 | 1.0 |
| *Peptococcum asaccharolyticus* 1302 | 4 | 0.25 | ≦0.125 | ≦0.125 | 0.25 |
| *Peptococcus prevoti* 1281 | 4 | 16 | 8 | 16 | 8 |
| *Peptostreptococcus anaerobium* 1451 | 1.0 | 16 | 8 | 16 | 8 |
| *Peptostreptococcus intermedius* 1264 | 1.0 | ≦0.125 | <0.125 | 0.25 | ≦0.125 |
| *Propionibacterium acnes* 79 | 4 | 8 | 2 | ≦0.125 | ≦0.125 |
| *Bacteroides fragilis* 111 | 16 | 16 | 16 | 32 | 16 |
| *Bacteroides fragilis* 1877 | 16 | 16 | 32 | 32 | 16 |
| *Bacteroides fragilis* 1936B | 16 | 16 | 16 | 32 | 16 |
| *Bacteroides thetaiotaomicron* 1438 | 16 | 16 | 8 | 16 | 8 |
| *Bacteroides malaninogenicus* 1856/28 | >64 | 16 | 16 | 32 | 16 |
| *Bacteroides malaninogenicus* 2736 | 16 | 16 | 16 | 64 | 32 |
| *Bacteroides vulgatis* 1211 | 8 | 16 | 16 | 32 | 8 |
| *Bacteroides corrodens* 1874 | 16 | 16 | 16 | 32 | 16 |
| *Fusobacterium symbiosum* 1470 | 1.0 | 8 | 8 | 16 | 8 |
| *Fusobacterium necrophorum* 6054A | 1.0 | 16 | 8 | 16 | 16 |

*MIC Determined by the Agar-Dilution Method, Endpoints Read After 24-Hr. incubation.
+Different lots of A84575 complex

TABLE 14

SUSCEPTIBILITY OF CLOSTRIDIUM DIFFICILE STRAINS

| STRAIN | MIC (μg/mL) | | | | |
|---|---|---|---|---|---|
| | Vancomycin | A84575+ | A84575+ | A84575+ | A84575F |
| 8484 | 2 | 0.125 | 0.125 | 0.25 | 0.125 |
| 6890 | 0.5 | 0.25 | 0.06 | 0.25 | 0.06 |
| 2634 | 0.5 | 0.06 | 0.06 | 0.125 | 0.06 |
| 78 | 4 | 0.25 | 0.25 | 0.5 | 0.125 |
| A-194 | 1.0 | 0.25 | 0.25 | 0.5 | 0.125 |
| A-195 | 0.5 | 0.06 | 0.125 | 0.125 | 0.25 |
| A-196 | 0.5 | 0.125 | 0.125 | 0.25 | 0.25 |
| A-279 | 0.5 | 0.125 | 0.125 | 0.125 | 0.125 |
| A-280 | 1.0 | 0.125 | 0.125 | 0.25 | 0.25 |
| A-281 | 1.0 | 0.25 | 0.25 | 0.25 | 0.125 |
| WAL-2112 | 1.0 | 0.25 | 0.25 | 0.25 | 0.25 |
| WAL-3657 | 2 | 0.25 | 0.25 | 0.25 | 0.125 |
| WAL-4268 | 1.0 | 0.125 | 0.125 | 0.125 | 0.125 |
| 107B | 0.25 | 0.06 | 0.06 | 0.125 | 0.25 |
| 111F | 1.0 | 2 | 4 | 4 | 0.125 |
| 1153 | 1.0 | 0.125 | 0.125 | 0.25 | 0.125 |
| 3424-5B | 1.0 | 4 | 0.25 | 0.25 | 0.125 |
| 3816 | 1.0 | 4 | 8 | 8 | 4 |
| 3950D | 0.5 | 0.25 | 0.25 | 0.25 | 0.125 |

*MIC Determined by the Agar-Dilution Method, Endpoints Read After 24-Hr. incubation.
+Different lots of A84575 complex

TABLE 15

SUSCEPTIBILITY OF PROPIONIBACTERIUM ACNES ISOLATES*

| STRAIN | MIC (μg/mL) | | | | |
|---|---|---|---|---|---|
| | Vancomycin | A84575+ | A84575+ | A84575+ | A84575F |
| *Propionibacterium acnes* #44 | 0.5 | 0.125 | 0.125 | 0.125 | 0.125 |
| *P. acnes* #8586A | 0.5 | 0.03 | 0.06 | 0.015 | 0.015 |
| *P. acnes* #5260 | 0.5 | 0.25 | 0.125 | 0.015 | 0.015 |
| *P. acnes* #103 | 0.25 | 0.03 | 0.06 | 0.125 | ≦0.008 |
| *P. acnes* #104 | 0.5 | 0.25 | 0.125 | 0.125 | 0.06 |
| *P. acnes* #105 | 0.25 | 0.125 | 0.125 | 0.06 | 0.03 |
| *P. acnes* #106 | 0.5 | 0.125 | 0.03 | 0.015 | 0.03 |
| *P. acnes* #107 | 0.25 | 0.06 | 0.06 | 0.125 | 0.03 |
| *P. acnes* #5292 | 0.5 | 0.03 | 0.06 | 0.125 | 0.03 |
| *P. acnes* #5170 | 0.25 | 0.03 | 0.06 | 0.125 | 0.03 |
| *P. acnes* #5176 | 2 | 0.5 | 0.25 | 0.5 | 0.5 |
| *P. acnes* #5187 | 0.5 | 0.25 | 0.125 | 0.25 | 0.125 |
| *P. acnes* #5191 | 0.5 | 0.125 | 0.06 | 0.125 | 0.03 |
| *P. acnes* #5197 | 0.5 | 0.125 | 0.06 | 0.125 | 0.06 |
| *P. acnes* #5226 | 0.5 | 0.06 | 0.03 | 0.06 | 0.03 |
| *P. acnes* #5227 | 0.25 | 0.125 | 0.125 | 0.25 | 0.03 |
| *P. acnes* #5228 | 0.25 | 0.06 | 0.03 | 0.03 | 0.015 |
| *P. acnes* #5229 | 0.25 | 0.125 | 0.06 | 0.015 | 0.03 |
| *P. acnes* #5246 | 0.25 | 0.06 | 0.06 | 0.015 | 0.015 |

*MIC Determined by the Agar-Dilution Method, Endpoints Read After 24-Hr. incubation.
+Different lots of A84575 complex

TABLE 16
SUSCEPTIBILITY OF ANEROBIC COCCI ISOLATES*

| ANAEROBIC COCCUS | MIC (µg/mL) | | | | |
|---|---|---|---|---|---|
| | Vancomycin | A84575+ | A84575+ | A84575+ | A84575F |
| Peptococcus asaccharolyticus WAL-3218 | 0.125 | 0.06 | 0.06 | 0.125 | 0.03 |
| Peptococcus variabilis ATCC-14956 | 0.125 | 0.06 | 0.06 | 0.125 | 0.03 |
| Peptococcus constellatus 1468 | 1.0 | 0.25 | 0.125 | 0.25 | 0.25 |
| Peptococcus magnus 1401 | 0.125 | 0.015 | 0.03 | 0.5 | 0.125 |
| Peptococcus magnus 1421 | 0.5 | 0.06 | 0.06 | 0.125 | 0.125 |
| Peptococcus magnus 29328 | 1.0 | 0.125 | 0.125 | 0.125 | 0.125 |
| Peptococcus prevoti 1281 | 2 | 1.0 | 0.5 | 0.5 | 1.0 |
| Peptococcus prevoti 1293 | 2 | 2 | 4 | 4 | 2 |
| Peptococcus prevoti 1407 | 2 | 2 | 1.0 | 1.0 | 2 |
| Peptostreptococcus anaerobius 8 | 1.0 | 1.0 | 0.5 | 1.0 | 0.5 |
| Peptostreptococcus anaerobius 52 | 1.0 | 0.5 | 0.125 | 0.5 | 0.5 |
| Peptostreptococcus anaerobius 59 | 0.25 | 0.03 | 0.5 | 1.0 | 0.125 |
| Peptostreptococcus anaerobius 1451 | 2 | 1.0 | 2 | 1.0 | 2 |
| Peptostreptococcus anaerobius 1428 | 0.03 | 0.25 | 0.015 | 0.25 | 0.25 |
| Peptostreptococcus anaerobius 1477 | 2 | 1.0 | 1.0 | 1.0 | 1.0 |
| Peptostreptococcus intermedius 1624 | 0.25 | 0.125 | 0.06 | 0.125 | 0.06 |
| Peptostreptococcus intermedius 1524 | 1.0 | 0.5 | 0.25 | 0.5 | 0.25 |
| Peptococcus asaccharolyticus 1302 | 1.0 | 0.125 | 0.125 | 0.25 | 0.125 |

*MIC Determined by the Agar-Dilution Method, Endpoints Read After 24-Hr. incubation.
+Different lots of A84575 complex

TABLE 17
In Vivo Activity of A84575 Antibiotics Administered Subcutaneously to Mice

| Antibiotic | Organism | $ED_{50}$ (mg/kg × 2) | LD Challenge |
|---|---|---|---|
| A84575 complex | Streptococcus pyogenes | 0.18 | 464 |
| A84575 complex | Streptococcus aureus | 0.23 | 631 |
| A84575 complex | Streptococcus pneumoniae | 0.94 | 587 |
| A84575B | Streptococcus pyogenes | 0.36 | 464 |
| A84575B | Streptococcus aureus | 0.38 | 631 |
| A84575B | Streptococcus pneumoniae | 1.90 | 587 |
| Vancomycin | Streptococcus pyogenes | 0.72 | 464 |
| Vancomycin | Streptococcus aureus | 0.83 | 631 |
| Vancomycin | Streptococcus pneumoniae | 1.58 | 587 |
| A84575F | Streptococcus pyogenes | 0.16 | 464 |
| A84575F | Streptococcus aureus | 0.20 | 631 |
| A84575F | Streptococcus pneumoniae | 0.42 | 587 | bacteria. The antimicrobial compounds can be administered orally, parenterally (for example, intravenously, intramuscularly or subcutaneously) or as a topical ointment or solution in treating bacterial infections of warm-blooded animals.

The term "pharmaceutically-acceptable salts" includes alkali and alkaline earth metal salts of the compounds of the present invention, for example, lithium, sodium, potassium, and calcium, as well as acid addition salts such as those which are formed between the compounds of the present invention and acids such as hydrochloric, hydrobromic, sulfuric and phosphoric acids.

In a further aspect, this invention relates to pharmaceutical compositions of the A84575 complex, an individual A84575 factor or any combination of the individual factors. These compositions are composed of a therapeutically active amount of the instant antibiotic compounds (i.e. the A84575 complex or factor A, factor B, factor C, factor D, factor E, factor F, factor G, or factor H separately or in combination) and a suitable vehicle.

TABLE 18
Plasma Levels of A84575 and Vancomycin in Mice[1]

| | Hours | | | | | | |
|---|---|---|---|---|---|---|---|
| | 0.08 | 0.33 | 0.66 | 1 | 2 | 4 | 8 |
| A84575 Complex | 0.59*[1] ± 1.32 | 2.92 ± 0.13 | 4.13 ± 1.21 | 3.37 ± 0.56 | 10.30*[2] + 7.82 | 8.49*[3] ± 8.78 | 2.77 ± 1.04 |
| Vancomycin | 5.84 ± 2.68 | 14.25 ± 7.8 | 7.47 ± 2.5 | 5.41 ± 2.4 | 0.87 ± 0.2 | NZ[b] | NZ |

[a]Injected subcutaneously into five ICR-Barrier mice (n = 5) at 20 mg/kg
[b]NZ = no zone
*[1]Only 1 zone out of 5  † standard deviation
*[2]One very high concentration in one animal; if average of remaining 4 animals, level = 7.07 ± 3.48
*[3]One very high concentration in one animal; if average of remaining 4 animals, level = 4.98 ± 4.5

TABLE 19
Plasma Levels of A84575 in Rats[a,c]

| | Hours | | | | | | | |
|---|---|---|---|---|---|---|---|---|
| | 0.08 | 0.33 | 0.66 | 1 | 2 | 4 | 8 | 12 |
| A84575 Complex | 158.29 ± 5.51 | 91.43 ± 18.76 | 61.44 ± 11.1 | 50.68 ± 8.71 | 39.08 ± 1.03 | 27.17 ± 8.28 | 3.38 ± 1.76 | NZ[b] |

[a]Injected intravenously into three Sprague-Dawley rats (n = 3) at 20 mg/kg
[b]NZ = no zone
[c]T½ = between 1.77 and 1.82 hr.

The A84575 complex, the individual factors and pharmaceutically-acceptable salts thereof of this invention are useful for the therapeutic or propylactic treatment of infections in mammals caused by pathogenic cle.

With regard to compositions for oral administration (for example tablets and capsules), the term "suitable vehicle" means common excipients such as binding agents, for example, syrup, acacia, gelatin, sorbitol, tragacanth, polyvinylpyrrolidine (Povidone), methyl cellulose, ethyl cellulose, sodium carboxymethyl cellulose, hydroxypropyl methyl cellulose, sucrose, and starch; fillers and carriers, for example corn starch, gelatin, lactose, sucrose, microcrystalline cellulose, kaolin, mannitol, dicalcium phosphate, sodium chloride, and aliginic acid, disintegrators such as croscarmellose sodium, microcrystalline cellulose, corn starch, sodium starch glycolate, aliginic acid, and mutable wetting agents such as sodium lauryl sulfate; and lubricants such as magnesium stearate and other metallic stearates, stearic acid, silicone fluid, talc, waxes, oils, and colloidal silica. Flavoring agents such as peppermint, oil of wintergreen, cherry flavoring or the like can also be used. It may be desirable to add a coloring agent to make the dosage form more appealing visually or to help identify the product. The tablets may also be coated by methods well known in the art.

The pharmaceutical compositions of the present invention may also be in the form of oral liquid preparations, which may be either a) aqueous or oily suspensions, solutions, emulsions or syrups; or b) a dry powder to be reconsistuted with water or another suitable vehicle before use. When used in conjunction with such oral liquid preparations, the term "suitable vehicle" means conventional additives such as suspending agents, for example, sorbitol, syrup, methyl cellulose, glucose/sugar syrup, gelatin, hydroxyethyl cellulose, carboxymethyl cellulose, or aluminum stearate gel; or hydrogenated edible oils, for example, almond oil, fractionated coconut oil, oily esters, propylene glycol or ethyl alcohol; and preservatives such as methyl or propyl p-hydroxybenzoates or sorbic acid.

The pharmaceutical composition can also be for intravenous (IV) use. Specifically, a water soluble form of the antibiotic compound can be dissolved in one of the commonly used intravenous fluids and administered by infusion. When used in conjunction with compositions for IV use, the term "suitable vehicle" means such fluids as physiological saline, Ringer's solution or 5% dextrose solution.

For intramuscular preparations a sterile formulation of a suitable salt form of the antibiotic compound (for example, the hydrochloride salt or sodium salt) can be formulated with a "suitable vehicle". Examples of such sterile formulations are a suitable salt form either dissolved in a pharmaceutical diluent (for example, Water-for-Injection, physiological saline, 5% glucose) or suspended in an aqueous base or a pharmaceutically acceptable oil base (for example, an ester of a long chain fatty acid such as ethyl oleate).

Topical compositions can be formulated with "suitable vehicles" such as hydrophobic or hydrophilic bases. Such bases include ointments, creams or lotions.

The antibiotic compounds of the instant invention can also be formulated in unit dosage form in sterile vials, sterile plastic pouches containing a part with a septum, or sterile, hermetically sealed ampoules. The antibiotic compound (or a pharmaceutically-acceptable salt thereof) may be a dry powder in crystalline or lyophilized form. The amount of the antibiotic compound per unit dosage may vary from about 250 milligrams to about 10 grams.

A "therapeutically effective amount" of the antibiotic compounds of the present invention is from approximately 3.5 mg to about 50 mg of compound per kilogram of body weight. This amount generally totals from about 1 gram to about 27 grams per day for an adult human.

A further aspect of this invention is a method for treating or controlling infectious diseases caused by bacteria in warm-blooded animals. This method comprises administering to the subject a therapeutically effective amount of the instant antibiotic compounds. A typical daily dose for an adult human in this method is from about 1 gram to about 12 grams.

In practicing this method, the antibiotic compound can be administered in a single daily dose or in multiple doses per day. The treatment regime may require administration over extended periods of time, for example, for several days or for from two to three weeks. The amount administered per dose or the total amount administered will depend on such factors as the nature and severity of the infection, the age and general health of the patient, and the tolerance to the antibiotic compound of both the patient and the microorganism or microorganisms involved in the infection.

The following examples are provided to further illustrate the invention. It is not intended that the invention be limited in scope by reason of any of the following examples.

EXAMPLE 1

Preparation of A84575 Complex

The culture *Streptosporangium carneum* NRRL 18505 was used as a submerged culture suspension maintained in liquid nitrogen to inoculate a seed medium having the following composition:

| Ingredient | Amount (g/L) |
| --- | --- |
| Glucose | 10.0 |
| Soluble Starch | 20.0 |
| Enzyme-hydrolyzed casein* | 5.0 |
| Yeast extract | 5.0 |
| CaCO$_3$ | 1.0 |
| Tap water q.s. to | 1 liter |

*N—Z-AMINE A, (standard broth ingredient known to those skilled in the art composed of enzyme-hydrolyzed casein) Humko Sheffield Chemical, Lyndhurst, NJ, USA The pH of the medium was adjusted to 7.2 with aqueous sodium hydroxide. The medium was autoclaved, after which the pH of the medium was 6.8.

The inoculated vegetative medium was incubated for 72 hours at 30° C. on a shaker rotating through an arc two inches in diameter at 250 RPM. The resulting vegetative medium culture was used either to inoculate small fermenters (the inoculum being approximately 1% per volume of fermenter medium), or to inoculate second stage flasks for the production of a larger volume of inoculum ("bump" medium).

EXAMPLE 2

Bump Medium

Two wide-mouth Erlenmeyer flasks (2 liter capacity) were charged with a medium (400 mL each) having the same composition as the vegetative culture medium.

The medium in each Erlenmeyer flask was inoculated with the above vegetative culture. The volume of the inoculum totaled 2.5% of the volume of the medium in the Erlenmeyer flask. The inoculated medium was incubated at 30° C. for 48 hours on a rotary shaker at 250 RPM to yield a "bump" culture.

EXAMPLE 3

Large Scale Fermentation

A portion of the above "bump" culture (800 mL) was used to inoculate the following medium (100 liter):

| Ingredient | Amount (g/L) |
|---|---|
| Antifoam* | 0.2 |
| Antifoam P-2000 | 0.1 |
| Glucose | 25.0 |
| Potato Dextrin | 35.0 |
| Soybean Grits | 15.0 |
| Casein | 5.0 |
| Blackstrap molasses | 6.0 |
| $CaCO_3$ | 2.5 |
| Tap water q.s. to | 110 liters |

*Dow-Corning ANTIFOAM SAG 471 ® (a standard antifoam agent used in culture media and known to those skilled in the art)

The medium was contained in a 165-liter fermenter. The pH of the medium was adjusted to 7.5 with 5N aqueous sodium hydroxide. The mixture was sterilized by the FO method. After the sterilization procedure, the medium had pH 7.0–7.2. The sterilized medium was aerated with sterile air at the rate of 0.125 v/v/m, stirred with a conventional agitator at controlled speeds to maintain the dissolved oxygen level at 40% of air saturation and allowed to ferment for about 6 days at a temperature of 32° C.

EXAMPLE 4

Isolation of the A84575 Antibiotic Complex

Whole broth fermentation, (220 liters), with a pH of 7.8 was filtered using 3% filter aid (HYFLOSUPERCEL, a diatomaceous earth, Johns-Manville Products Corporation) in a filter press. The biomass was washed with 45 liters of water and the washwater combined with the filtrate. To the combined filtrate and wash (235 liters) were added 14 liters of DIAION HP-20 resin (a highly porous styrene-divinylbenzene copolymer in bead form, Mitsubishi Chemical Industries, Limited, Tokyo, Japan) and stirred at room temperature for two hours.

The resin was then placed into a glass column and eluted with methanol:water - two column volumes of (1:3) and five column volumes of (3:1). Each fraction (4 liters each) was analyzed for its biological activity. The bioassay was performed by a paper disc assay on agar plates seeded with *Bacillus subtilis*; the procedure was repeated using agar plates seeded with *Micrococcus luteus*.

The bioactive fractions were combined, concentrated under reduced pressure to a volume of two liters and filtered to give a first crop precipitate of complex. The pH of the filtrate was adjusted to 3.0 using 5M HCl and left standing at 4° C. for 16 hours. The precipitate that formed was removed by filtration, washed using water, and dried to give 15.4 grams of a second crop of A84575 complex.

Example 5

Isolation of Factors A,B, and C

First crop precipitate, prepared as described in Example 4, was dissolved into one liter of methanol at pH 3.0, filtered, concentrated to a volume of 50 mL and applied to a 5.2×92 cm glass column packed with LH-20 SEPHADEX (Pharmacia Fine Chemicals, Piscataway, N.J., USA), prepared in methanol. (SEPHADEX is a polysaccharide polymer in form of beads used for separation of molecules by size.) The column was developed with methanol. Each of the 25-ml fractions collected was analyzed for its biological activity as described in the previous example. Fractions 26–42 were combined, concentrated to a residue, dissolved into dioxane/water and lyophilized to give 4.2 grams of a partly purified active antibiotic complex. This material was dissolved into two liters of water at pH 8.0 using 2M NaOH, and applied to a 2.2×25-cm glass column packed with DEAE SEPHADEX A-25 ($OH^-$)(Pharmacia). The column was washed with two liters of water at pH 8.0 and then eluted with different concentrations of $NaCl/NH_4OH$ in water.

The following 25-mL fractions were collected:

| Fraction | Solvents |
|---|---|
| 1–30 | 0.2M NaCl + 0.05M $NH_4OH$, in water |
| 31–50 | 0.4M NaCl + 0.10M $NH_4OH$, in water |
| 51–90 | 0.8M NaCl + 0.20M $NH_4OH$, in water |

Fractions 37–46 were combined, desalted on HP-20, concentrated and lyophilized to give 663 mg of a partly purified antibiotic preparation.

This material was dissolved into 600 ml of water and applied to a 1.7×6.5-cm column packed with activated AFFl-GEL-15 (Bio-Rad Laboratories, Richmond, Calif.) in water, and the following fractions were collected:

| Fraction | Vol (mL) | Eluent |
|---|---|---|
| 1 | 125 | effluent |
| 2 | 125 | " |
| 3 | 125 | " |
| 4 | 125 | " |
| 5 | 125 | " |
| 6 | 100 | water |
| 7 | 100 | 0.01N HCl, in water |
| 8 | 100 | 0.01N HCl, water; $CH_3OH$ (3:1) |
| 9 | 100 | 0.01N HCl, water: $CH_3OH$ (1:1) |
| 10 | 100 | 0.05N $NH_4OH$, water; $CH_3OH$ (1:1) |

Fractions 2–5 were combined, added to 50 mL of 1M $NH_4OAc$ at pH 5.5, and applied to a 1.7×6.5-cm column of AFFl-GEL-15 packed with 0.1M $NH_4OAc$ at pH 5.5. Fractions were monitored by biological assay and HPLC.

The following fractions were collected:

| Fraction | Vol (mL) | Eluent |
|---|---|---|
| 1 | 125 | effluent |
| 2 | 125 | " |
| 3 | 125 | " |
| 4 | 125 | " |
| 5 | 125 | " |
| 6 | 100 | 0.1M $NH_4OAc$, pH 5.5 |
| 7 | 100 | 0.01M HCl, water |
| 8 | 100 | 0.01M HCl:$CH_3OH$ (3:1) |
| 9 | 100 | 0.01M HCl:$CH_3OH$ (1:1) |
| 10 | 100 | 0.05M $NH_4OH$:$CH_3OH$ (1:1) |

Fraction 10 was neutralized, added to four volumes of water and de-salted on HP-20 (Mitsubishi), concentrated, and lyophilized to give 125 mg of a purified preparation containing factors A, B, and C This material was dissolved in 4.0 mL of the packing solvent described infra and chromatographed on a MICHEL-MILLER glass column (Ace Glass Inc. Vineland, USA) packed with 15-25 micron LI-CHRO-PREP RP-18 (a standard reverse phase column known to those skilled in the art, EM Science, a Division of EM industries; Inc., Cherry Hill, USA), in 0.05M NH$_4$OAc:methanol (6:4) at pH 7.5. The column was developed using a linear gradient of 1.0 liter of 0.05M NH$_4$OAc:methanol (6:4) at pH 7.5 to 1.0 liter of 0.05M NH$_4$OAc:methanol (1:1) at pH 7.5. A 250-mL fraction was collected first and 20-mL fractions thereafter at a flow rate of 5 ml/minute. Fractions 14-24 were combined, added to 1.5 volumes of water, de-salted on HP-20 as described supra, and lyophilized to give 17 mg of A84575A. Fractions 41-45, worked up by an identical procedure, gave 21 mg of A84575B; and fractions 50-54 gave 11 mg of A84575C.

EXAMPLE 6

Isolation of Factors D, E, F, G, and H

Factors D, E, F, G, and H were obtained in quantities sufficient for chemical characterization and biological testing using additional solutions and precipitates from the antibiotic complex work-up. Specifically, each factor was isolated upon elution from the disclosed chromatographic system according to retention times disclosed supra.

We claim:

1. A biologically pure culture of *Streptosporangeum carneum* selected from the group consisting of NRRL 18437, NRRL 18505, and mutants of said cultures which produce A84575 compounds.

* * * * *